(12) United States Patent
Hoff et al.

(10) Patent No.: US 7,659,101 B2
(45) Date of Patent: Feb. 9, 2010

(54) ALKALINE *BACILLUS* AMYLASE (75) Inventors: Tine Hoff, Holte (DK); Shamkant Anant Patkar, Lyngby (DK); Jeppe Wegener Tams, Gentofte (DK)

(73) Assignee: Novozymes A/S, Bagsvaerd (DK)

( * ) Notice: Subject to any disclaimer, the term of this patent is extended or adjusted under 35 U.S.C. 154(b) by 396 days.

(21) Appl. No.: 11/721,353

(22) PCT Filed: Dec. 15, 2005

(86) PCT No.: PCT/DK2005/000794

§ 371 (c)(1),
(2), (4) Date: Jun. 11, 2007

(87) PCT Pub. No.: WO2006/063594

PCT Pub. Date: Jun. 22, 2006

(65) Prior Publication Data

US 2009/0239284 A1 Sep. 24, 2009

Related U.S. Application Data (60) Provisional application No. 60/636,212, filed on Dec. 15, 2004.

(30) Foreign Application Priority Data

Dec. 15, 2004 (DK) .............................. 2004 01936

(51) Int. Cl.
*C12N 9/28* (2006.01)
*C12N 1/20* (2006.01)
*C07H 21/04* (2006.01)
*C11D 3/386* (2006.01)

(52) U.S. Cl. ............... 435/202; 435/252.3; 435/252.33; 435/254.1; 435/320.1; 536/23.2; 536/23.1; 510/114

(58) Field of Classification Search ........................ None
See application file for complete search history.

(56) References Cited

FOREIGN PATENT DOCUMENTS

| WO | WO 00/56447 | 10/1990 |
|---|---|---|
| WO | WO 95/26397 | 10/1995 |
| WO | WO 96/23873 | 6/1996 |
| WO | WO 99/50399 | 10/1999 |
| WO | WO 01/14532 | 3/2001 |

OTHER PUBLICATIONS

XP002377812, Accession No. Q9KFR4—Abstract (2000).
XP008044903, Takami et al., "Complete Genome Sequence of the Alkaliphilic Bacterium *Bacillus halodurans* and Genomic Sequence Comparison *Bacillus subtilis*" Nucleic Acids Research, Oxford University Press, Surrey, GB, vol. 28. No. 21, pp. 4317-4331 (2000).
XP002377813, Takami and Takaki, " *Bacillus halodurans* C-123 DNA", Accession No. BA000004—Abstract (2004).
XP002377814, Takaki et al., "*Bacillus clausii*", Accession No. Q5WHK9 (2004).
XP002145563, Shirokizawa et al., "Nucleotide Sequence of the G-6 Amylase Gene from Alkalophilic *Bacillus*-SP H-167" Fems Microbiology Letters, Amsterdam, NL, vol. 70, No. 2, pp. 131-136 (1990).
XP000026624, Shirokizawa et al., "Cloning and Expression of the Malthohexaose-Forming Amylase Gene from Alkalophilic *Bacillus* SP. H-167 in *Escherichia coli*" Agricultural and Biological Chemistry, Japan Soc. For Bioscience, Biotechnology and Agrochem. Tokyo, JP, vol. 53, No, 2, pp. 491-495 (1989).
XP001203463, Nielsen et al., "Phenetic Diversity of Alkaliphilic *Bacillus* Strains: Proposal for Nine New Species" Microbiology, Society for General Microbiology, Reading, GB, vol. 141, No. 7. pp. 1745-1761 (1995).
XP002377542, Horikoshi Koki, "Alkaliphiles: from an Industrial Point of View" Fems Microbiology Reviews, vol. 18. No. 2-3. pp. 259-270 (1996).
M. Takagi et al., "Diversity In Size And Alkaliphily of Thermostable" J.Ferment. Bioeng , vol. 81, 6:557-559 (1996).
International Search Report dated Apr. 11, 1996 for WO2006/063594.

*Primary Examiner*—Nashaat T Nashed
(74) *Attorney, Agent, or Firm*—Michael W. Krenicky (57) ABSTRACT

This invention relates to an amylase derived from *Bacillus horikoshii*. The amylase has a preference for soluble substrates, shows substantial exo-amylase activity and has a pH optimum of about 9.8.

18 Claims, 3 Drawing Sheets

ALKALINE *BACILLUS* AMYLASE

CROSS-REFERENCE TO RELATED APPLICATIONS

This application is a 35 U.S.C. 371 national application of PCT/DK2005/000794 filed Dec. 15, 2005, which claims priority or the benefit under 35 U.S.C. 119 of Danish application no. PA 2004 01936 filed Dec. 15, 2004 and U.S. provisional application No. 60/636,212 filed Dec. 15, 2004, the contents of which are fully incorporated herein by reference.

FIELD OF THE INVENTION

The present invention relates to amylases having a pH optimum around 9.8.

BACKGROUND OF THE INVENTION

For a number of years alpha-amylase enzymes have been used for a variety of different purposes, the most important of which are starch liquefaction, textile desizing, starch modification in the paper and pulp industry, and for brewing and baking.

Examples of commercial alpha-amylase products are Termamyl®, BAN® and Fungamyl®, all available from Novozymes A/S, Denmark. These and similar products from other commercial sources have an acidic to a neutral pH optimum, typically in the range of from pH 5 to pH 7.5, and they do not display optimal activity in detergent solutions at alkaline pH.

WO 95/26397 discloses an alpha-amylase from a *Bacillus* strain, which has optimum activity at pH 8. WO 96/23873 describes variants of *Bacillus* amylases with improved performance under washing conditions.

U.S. Pat. No. 5,147,796 describes an alkaline pullulanase having alpha-amylase activity. FIG. 2*b* of the document shows optimum amylase activity at pH 8-8.5.

M. Takagi et al., J. Ferment. Bioeng, vol 81, No. 6, 557-559 (1996) describe an alkaliphilic alpha-amylase-pullulanase from *Bacillus* sp. The enzyme has optimum amylase activity at pH 9, but the activity drops rapidly at higher pH, and the activity at pH 10 is lower than at pH 7.

WO 01/14532 and WO 99/50399 disclose alpha-amylases from *Bacillus* strains, which have optimum activity at pH 9.5.

The amylase of the present invention has a highly alkaline profile with an optimum activity at pH 9.8

SUMMARY OF THE INVENTION

The invention provides an alpha-amylase having one or more of the following characteristics:
  a) An amino acid sequence which has at least 60% identity with amino acids 1 to 1105 of Seq Id No: 2.
  b) An amino acid sequence comprising Seq Id No: 2.
  c) An amino acid sequence that is identical to Seq Id No: 2.
  d) An amino acid sequence comprised by Seq Id No: 2

In a further aspect the invention relates to an alpha-amylase having one or more characteristics selected from the group consisting of:
  a) a theoretical pI of about 4.4; or
  b) a pH-optimum of about 9.8; or
  c) a temperature optimum of about 50° C. at pH 9; or
  d) at least 40% residual activity after 30 minutes at 50° C. and pH 10; or
  e) exhibits substantial exo-amylase activity
  f) obtainable from *Bacillus horikoshii*.

In a further aspect the invention relates to an alpha-amylase encoded by a polynucleotide which hybridizes under medium stringency conditions, more preferably high stringency conditions, with the nucleic acid sequence of Seq Id No: 1 or its complementary strand.

In a still further aspect the invention relates to a DNA sequence encoding the alpha-amylase of the invention. In a particular embodiment said DNA sequence comprises or is comprised by Seq. ID No: 1.

Further aspects of the invention provide a recombinant expression vector comprising the DNA sequence, and a cell transformed with the DNA sequence or the recombinant expression vector.

The invention also provides a method for producing the alpha-amylase and for the use of said alpha-amylase for production of malto-oligosaccharides with a DP of less than 10, and as a detergent enzyme.

DETAILED DESCRIPTION OF THE INVENTION

Sequence Listing and Deposited Microorganisms

The present application contains information in the form of a sequence listing, which is appended to the application and also submitted on a data carrier accompanying this application. In addition, the present application refers to deposited microorganisms. The contents of the data carrier and the deposited microorganisms are fully incorporated herein by reference.

The alpha-amylase of the invention may be derived from *Bacillus* sp. strain NCIB 12512. This strain was deposited on 29 Jul. 1987 under the terms of the Budapest Treaty on the International Recognition of the Deposit of Microorganisms for the Purposes of Patent Procedure at the National Collections of Industrial and Marine Bacteria Limited (NCIMB), 23 St. Machar Drive, Aberdeen AB2 1RY, Scotland, United Kingdom.

The deposit was made by Novo Nordisk A/S and was later assigned to Novozymes A/S.

Production of Alpha-Amylase

The alpha-amylase of the invention can be produced by cultivating a suitable amylase-producing strain of *Bacillus* or the transformed host cell of the invention in a suitable nutrient medium, and recovering the alpha-amylase from the culture medium.

The medium used to cultivate the cells may be any conventional medium suitable for growing the host cell in question and obtaining expression of the alpha-amylase of the invention. Suitable media are available from commercial suppliers or may be prepared according to published recipes (e.g. as described in catalogues of the American Type Culture Collection).

The alpha-amylase secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Properties of Alpha-Amylase

A preferred alpha-amylase is derived from *Bacillus horikoshii*. It can be produced as described in the examples. The full length amino acid sequence of the amylase and the DNA encoding it are shown in Seq. ID No. 2 and Seq. ID No. 1 respectively.

In the present context, "derived from" is intended not only to indicate an alpha-amylase produced or producible by a strain of the organism in question, but also an alpha-amylase encoded by a DNA sequence isolated from such strain and produced in a host organism trans-formed with said DNA sequence. Finally, the term is intended to indicate an alpha-amylase, which is encoded by a DNA sequence of synthetic and/or cDNA origin and which has the identifying characteristics of the alpha-amylase in question.

The following characteristics were found for the amylase of the invention (purified alpha-amylase):

A molecular weight of approximately 130 kDa as determined by SDS-PAGE using a Novex, 4-20% gradient gel. The theoretical MW of the polypeptide chain is 123 kDa, using the pc program GPMAW (Lighthouse data).

A theoretical pI of 4.4 was determined by the pc program Vector NTI 8, 1994-2002 Infomax, Inc.

Figure 1:
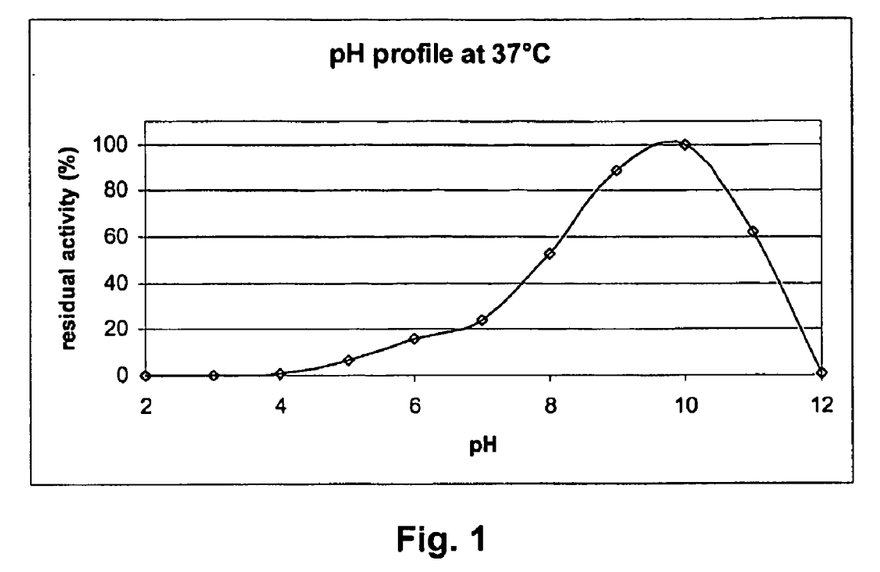
FIG. 1 shows a pH activity profile of the alpha-amylase of the invention.

A pH-activity curve is shown in FIG. 1, taking the activity at pH 9.8 as 100%. It was determined using the reducing sugar assay (PAHBAH) using 50 mM Britten-Robinson buffer adjusted to various pH-values. FIG. 1 shows that the optimum activity is about pH 9.8.

Figure 2:
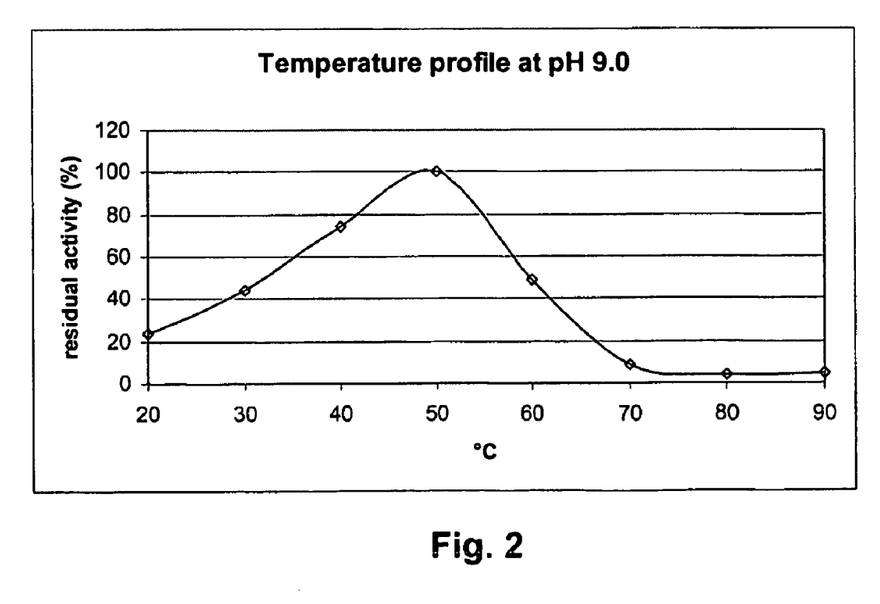
FIG. 2 shows a temperature activity profile of the alpha-amylase of the invention.

A temperature-activity curve was measured using the PAHBAH assay at various temperatures with 50 mM Britten-Robinson buffer adjusted to pH 9.0. The results are shown in FIG. 2. It is seen from FIG. 2 that the amylase of the invention has optimum activity at about 50° C. Temperature stability of the amylase was measured at pH 10. A stability profile of the amylase of the invention (FIG. 3) shows superior stability of the amylase of the invention compared to a commercial amylase.

pH stability of the amylase was measured at 37° C. A stability profile of the amylase of the invention (FIG. 4) shows superior stability of the amylase of the invention compared to a commercial amylase.

Sequence Homology and Alignment

For purposes of the present invention, alignments of sequences and calculation of homology and identity scores may be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Alignment may be made with the FASTA package version v20u6 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA", Methods in Enzymology, 183:63-98).

Multiple alignments of protein sequences may be made using "ClustalW" (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680). Multiple alignments of DNA sequences may be done using the protein alignment as a template, replacing the amino acids with the corresponding codon from the DNA sequence.

The amino acid sequence of the present invention exhibits a degree of identity preferably of at least 60%, or at least 65%, or at least 70%, or at least 75%, preferably at least 80%, or at least 85%, more preferably at least 90%, especially at least 95%, even more especially at least 96%, or at least 97%, or at least 98%, or at least 99% with the amino acid sequence shown in positions 1-1105 of SEQ ID NO: 2.

The DNA construct of the present invention comprises a DNA sequence exhibiting a degree of identity preferably of at least 60%, preferably at least 70%, more preferably at least 80%, especially at least 90% or at least 95%, even more especially at least 97% or at least 99% with the nucleic acid sequence shown in positions 109-3423 of SEQ ID NO: 1.

Hybridization

Suitable experimental conditions for determining hybridization between a nucleotide probe and a homologous DNA or RNA sequence involves presoaking of the filter containing the DNA fragments or RNA to hybridize in 5×SSC (sodium chloride/sodium citrate, Sambrook, et al., 1989) for 10 min, and prehybridization of the filter in a solution of 5×SSC, 5×Denhardt's solution (Sambrook, et al., 1989), 0.5% SDS and 100 µg/ml of denatured sonicated salmon sperm DNA (Sambrook, et al., 1989), followed by hybridization in the same solution containing a random-primed (Feinberg, A. P. and Vogelstein, B. (1983) Anal. Biochem. 132:6-13), 32P-dCTP-labeled (specific activity>1×10$^9$ cpm/µg) probe for 12 hours at ca. 45° C. The filter is then washed twice for 30 minutes in 2×SSC, 0.5% SDS at least 55° C. (low stringency), preferably at least 60° C. (medium stringency), more preferably at least 65° C. (medium/high stringency), more preferably at least 70° C. (high stringency), even more preferably at least 75° C. (very high stringency).

Molecules which hybridize to the oligonucleotide probe under these conditions are detected by exposure to x-ray film.

Recombinant Expression Vector

The present invention also relates to recombinant expression vectors comprising a polynucleotide of the present invention, a promoter, and transcriptional and translational stop signals. The various nucleic acids and control sequences described above may be joined together to produce a recombinant expression vector which may include one or more convenient restriction sites to allow for insertion or substitution of the nucleotide sequence encoding the polypeptide at such sites. Alternatively, a nucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al.: Molecular Cloning: A Laboratory Manual, Second Edition (1989) Cold Spring Harbor Laboratory Press, Cold Spring Harbor, N.Y.).

Host Cells

The cell of the invention, either comprising a DNA construct or an expression vector of the invention as defined above, is advantageously used as a host cell in the recombinant production of the alpha-amylase of the invention. The cell may be transformed with the DNA construct of the invention encoding the amylase, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be trans-formed with an expression vector as described above in connection with the different types of host cells.

The cell of the invention may be a cell of a higher organism such as a mammal or an insect, but is preferably a microbial cell, e.g., a bacterial or a fungal (including yeast) cell. Examples of bacterial host cells which, on cultivation, are capable of producing the enzyme of the invention are gram positive bacteria such as strains of *Bacillus*, such as strains of *B. subtilis, B. licheniformis, B. lentus, B. clausii, B. brevis, B. stearothermophilus, B. alkalophilus, B. amyloliquefaciens, B. coagulans, B. circulans, B. lautus, B. megaterium* or *B. thuringiensis*, or strains of *Streptomyces*, such as *S. lividans* or *S. murinus*, or gram negative bacteria such as *Escherichia coli*. The transformation of the bacteria may be effected by protoplast transformation, electroporation, conjugation, or by using competent cells in a manner known per se (cf. Sambrook et al., 1989: Molecular Cloning: A Laboratory Manual, Second Edition (1989) Cold Spring Harbor Laboratory Press, Cold Spring Harbor, N.Y.).

The yeast organism may favourably be selected from a species of *Saccharomyces* or *Schizosaccharomyces*, e.g. *Saccharomyces cerevisiae*. The filamentous fungus may advantageously belong to a species of *Aspergillus*, e.g., *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells is described in EP 238 023.

Industrial Applications—Please Provide Information about Relevant Applications

Owing to their activity at alkaline pH values, the alpha-amylases of the invention are well suited for use in a variety of industrial processes, e.g. laundry and hard surface cleaning detergent compositions, the production of sweeteners and ethanol from starch. Thus, it may be used in conventional starch-converting processes, such as liquefaction and saccharification processes described in U.S. Pat. No. 3,912,590 and EP patent publications Nos. 252,730 and 63,909.

Pulp and Paper Production

The alkaline alpha-amylase of the invention may also be used in the production of lignocellulosic materials, such as pulp, paper and cardboard, from starch reinforced waste paper and cardboard, especially where repulping occurs at pH above 7 and where amylases can facilitate the disintegration of the waste material through degradation of the reinforcing starch. The alpha-amylase of the invention is especially useful in a process for producing a papermaking pulp from starch-coated printed-paper. The process may be performed as described in WO 95/14807, comprising the following steps:

a) disintegrating the paper to produce a pulp, b) treating with a starch-degrading enzyme before, during or after step a), and c) separating ink particles from the pulp after steps a) and b).

The alpha-amylases of the invention may also be very useful in modifying starch where enzymatically modified starch is used in papermaking together with alkaline fillers such as calcium carbonate, kaolin and clays. With the alkaline alpha-amylases of the invention it becomes possible to modify the starch in the presence of the filler thus allowing for a simpler integrated process.

Desizing

The alpha-amylase of the invention may also be very useful in textile desizing. In the textile processing industry, alpha-amylases are traditionally used as auxiliaries in the desizing process to facilitate the removal of starch-containing size, which has served as a protective coating on weft yarns during weaving. Complete removal of the size coating after weaving is important to ensure optimum results in the subsequent processes, in which the fabric is scoured, bleached and dyed. Enzymatic starch break-down is preferred because it does not involve any harmful effect on the fibre material. In order to reduce processing cost and increase mill throughput, the desizing processing is sometimes combined with the scouring and bleaching steps. In such cases, non-enzymatic auxiliaries such as alkali or oxidation agents are typically used to break down the starch, because traditional alpha-amylases are not very compatible with high pH levels and bleaching agents. The non-enzymatic breakdown of the starch size does lead to some fibre damage because of the rather aggressive chemicals used. Accordingly, it would be desirable to use the alpha-amylases of the invention as they have an improved performance in alkaline solutions. The alpha-amylases may be used alone or in combination with a cellulase when desizing cellulose-containing fabric or textile.

Beer Making

The alpha-amylases of the invention may also be very useful in a beer-making process; the alpha-amylases will typically be added during the mashing process.

Production of Malto-Oligosaccharides

The alpha-amylase of the invention exhibits substantial exo-alpha-amylase (see break down pattern of amylase and waxy corn starch, Example 4). This allows for the use of the enzyme of the present invention for production of malto-oligosaccharides of a specific degree of polymerisation (DP), a process that otherwise is tedious and expensive. Malto-oligosaccharides with a DP around 10 or less have potential applications in e.g. the food industry. These malto-oligosaccharides have a less sweet taste compared to sucrose's, and a partial replacement of sucrose with e.g. maltotetraose (DP=4) reduces the sweetness of the foods without affecting their inherent taste and flavour. At the same time they have a high moisture retention power, and can thus serve to prevent retrogradation of starch ingredient and makes retain a suitable moisture in foods. A further aspect of application of malto-oligosaccharides is that they show a less Maillard reaction, and thus less coloration. Malto-oligosaccharides show higher viscosity than that of sucrose, and are useful in improving the texture of foods. A further aspect of the application of malto-oligosaccharides is that they may be used to control the freezing points of frozen foods, as they depresses the freezing point of water more moderately than sucrose or high-fructose syrup.

Detergent Compositions

The alpha-amylase of the invention may be added to and thus become a component of a detergent composition.

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the enzyme of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, a pectate lyase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The present invention is further described by the following examples, which should not be construed as limiting the scope of the invention.

Materials and Methods 50 mM Britton-Robinson Buffer 50 mM acetic acid, 50 mM phosphoric acid, 50 mM boric acid, pH adjusted to the value of interest with NaOH.

Detergent:

Commercial European color detergent; alpha-amylases present in the detergent were inactivated by microwaves before adding the alpha-amylase of the present invention.

EXAMPLES

Example 1

Cloning and Expression of the Alpha-Amylase of the Invention

Bacterial Strains and Growth Conditions

TH1 is a *Bacillus subtilis* strain (amy-, spo-, apr-, npr-), that has been modified by insertion of a construct, from the strain DN3 (Noone et al. 2000, J Bacteriol 182 (6) 1592-1599) by transformation and selection for erythromycin. The changed genotype is: ykdA::pDN3 (PykdA-lacZ Pspac-ykdA) Ermr. TH1 contains the following features: the full ykdA promoter is fused to the LacZ reporter gene. In addition the ykdA gene is placed under control of the IPTG-inducible Pspac promoter, so the ykdA gene no longer has it's naturally regulation. The strain can be used as host for expression clones and libraries and transformants expressing and secreting protein can be selected on plates containing X-gal and IPTG. TH1 can be maintained and propagated in Luria-Bertani (LB) or supplemented with agar (1.5% wt/vol) as appropriate, addition of 6 μg/ml erythromycin and grown at 37° C. with aeration.

DNA Manipulations

*Bacillus subtilis* transformations were performed as described previously (Anagnostopolous, C., and J. Spizizen. 1961. Requirements for transformation in *Bacillus subtilis*. J. Bacteriol. 81:741-746). All routine molecular biological procedures were performed according to the protocols described by Sambrook et al. (1989).

Modification of Vector

The shuttle vector for *Bacillus* and *E. coli* pDG268neo (Widner B; Thomas M; Sternberg D; Lammon D; Behr R; Sloma A (2000): Development of marker-free strains of *Bacillus subtilis* capable of secreting high levels of industrial enzymes. Journal of Industrial Microbiology and Biotechnology, Vol. 25 (4) pp. 204-212) was modified to allow for cloning of partial digested Sau3A or Tsp509I genomic DNA. The vector was modified by inserting a BamHI and EcoRI site between the Sac1 and Not1 sites (fragment between was deleted and a linker was inserted). In this way genomic fragments can be cloned and genes contained in these fragments can be transcribed from either the strong promoter on the vector or by their own promoter.

Construction of a Library in *E. coli*

Chromosomal DNA from *Bacillus horikoshii* was isolated by QIAmp Tissue Kit (Qiagen, Hilden, Germany). The genomic DNA was partial digested by Sau3A by standard methods. DNA fragments from 3-5 kb were gel purified and ligated into BamHI digested and dephosphorylated vector (the modified pDG268neo (=pDG268BE)). 1 micro L of the ligation was trans-formed by electroporation into competent *E. coli* cells (Electromax DH10B Cells, Invitrogen) according to standard protocols. The transformed cells were plated on plates containing solid LB media containing ampicillin as selection marker. The plates were incubated for 16 h at 37 C. 20.000 transformants obtained this way were pooled and plasmid DNA was prepared from the pooled cells by using a midiprep Qiagene kit (Qiagene). This plasmid pool represents the library.

Transformation of Library into *Bacillus subtilis* TH1

The obtained plasmid pool DNA was used to transform *Bacillus* TH1 competent cells. *Bacillus* transformations were plated on Petri dishes with LB-media supplemented with agar (1.5% wt/vol) and X-Gal (5-bromo-4-chloro-3-indolyl-b-D-galactopyranoside) was added to the media at a concentration of 64 micro g/mL, and IPTG (isopropyl-b-D-thiogalactopyranoside) was added to a final concentration of 0.8 mM. Antibiotics were added at the following concentrations: chloramphenicol, 6 μg/ml; and erythromycin, 3 μg/ml. Transformants were incubated at 37° C. overnight.

Selection and Analysis of Transformants Secreting Recombinant Protein

Blue colonies that occurred after 16 h of incubation or in the following 24 h were selected and restreaked on new plates to obtain pure single blue colonies. For expression studies transformants were grown in liquid PS-1 or TY media at 30° C. and at 250 rpm. Cells were spun down and the supernatant analysed for secreted recombinant protein on SDS-polyacrylamide gels.

Results

A genomic library of *Bacillus horikoshii* was made in the vector pDGneo268BE. A plasmid pool was made from the *E. coli* library. The plasmid pool DNA was transformed into *Bacillus* strain TH1 (TH1 allows for blue/white selection of secreting recombinant clones). 16-20000 *Bacillus* transformants were obtained on agar plates containing X-gal and IPTG, which allows for blue/white selection of secreting *Bacillus* transformants. Nineteen intense blue colonies appeared among the 16-20.000 colonies. These blue colonies were fermented in liquid media and the supernatants analysed on SDS-gels. 5 of the 19 blue colonies gave an intense protein band on a SDS gel. A recombinant protein band of around 120 kD from one of the clones was purified and characterised by N-terminal amino acid sequencing. The DNA insert in the corresponding clone was sequenced to identify the gene giving rise to the recombinant protein band. The resulting gene sequence is the sequence of the alpha amylase of the invention listed as the Seq. ID No:1 and the encoded protein is listed as the Seq. ID No: 2.

Example 2

Purification Method for the Alpha-Amylase of the Invention

The culture supernatant was centrifuged and cell debris was discarded.

Fermentation supernatant was then sterile filtered using Seitz-EKS filter with pore size 0.22 microns which was purchased from Pall Seitz Schenk Filter system GmbH, Bettringer Strasse 42 D-73550 Germany. Filtration was carried out using pressure filter.

The sterile filtered supernatant was then adjusted to 1 M ammonium sulphate by adding solid ammonium sulphate.

Hydrophobic chromatography on Matrix Phenyl Toyopearl 650M Toshohaas was purchased from Bie and Berntsen Roedovre, Denmark.

Fifty milliliter column was packed with the matrix and equilibrated with 1M ammonium sulphate adjusted to pH 8. Sterile filtered fermentation supernatant was then applied on the column and washed with the 1 Molar ammonium sulphate solution till all unbound material was washed out.

Bound Proteins were then eluted by lowering the salt concentration using 50 mM Borate pH 8 solution without any salt. Fractions 10 ml each were collected and analysed by SDS-PAGE.

Fractions containing protein with 120 kDa molecular weight were then pooled and dialyzed against Buffer containing 50 mM Borate, 5 mM Dimethyl glutaric acid pH 6.

Anion exchange chromatography on Fast flow Q sepharose matrix was purchased form Amersham Pharmacia and 50 ml column was packed. The column was then equilibrated with the buffer containing 50 mM Borate, 5 mM Dimethyl glutaric acid pH6. The dialyzed pool containing the 120 kDa protein was then applied on the column and washed with the buffer till all unbound material was washed out. The bound protein was then eluted with linear salt gradient using Buffer B pH6 which contained 50 mM Borate, 5 mM Dimethyl glutaric acid and 1 M salt.

Fractions were then analyzed by SDS-PAGE and pooled on the basis of Molecular weight which contained the desired protein.

Example 3

Characterisation of the Alpha-Amylase of the Present Invention

Reducing Sugar Assay (PAHBAH)

The enzyme reaction was initiated by adding 50 μl enzyme sample to 100 micro L 0.15% amylose (Merck, 4561), 50 mM Britton-Robinson buffer (50 mM acetic acid, 50 mM phosphoric acid, 50 mM boric acid, pH adjusted to the value of interest with NaOH), 0.01% Triton-X-100 in PCR tubes. This solution was incubated for 15 min at different temp. in a Peltier Thermal Cycler (PCT-200, MJ research) and stopped with 75 micro L 1.5% (w/v) p-hydroxybenzoic acid hydrazide (Sigma, H-9882), 5% (w/v) K—Na-tartrate (Merck, 1.08087), 2% (w/v) NaOH and incubated at 95° C. for 10 min. The temperature was lowered to 20° C. and 150 micro L was transferred to a 96 well micro titter plate. The absorbance was then measured at 410 nm with a microplate reader (Spectra Max 190, Molecular Devices).

pH Profile

The pH profile was measured at 37° C., at pH 2, 3, 4, 5, 6, 7, 8, 9, 10, 11 and 12 using the Reducing sugar assay described above.

The pH profile is shown in FIG. 1, and it is seen that the alpha-amylase of the invention has an optimum activity at about 9.8.

Temperature Profile

The temperature profile was measured at pH 9 at 20° C., 30° C., 40° C., 50° C., 60° C., 70° C., 80° C., 90° C. using the Reducing sugar assay described above.

The temperature profile is shown in FIG. 2, and it is seen that the alpha-amylase of the invention has an optimum activity at about 50° C.

Temperature Stability 150 micro L enzyme sample (diluted with 50 mM Britton-Robinson buffer: 50 mM acetic acid, 50 mM phosphoric acid, 50 mM boric acid, pH adjusted to 10 with NaOH, with 1 mM EDTA or 1 mM $CaCl_2$) in an Eppendorf tube was incubated for 30 min a in Eppendorf Thermomixer at different temperatures and 300 rpm shaking. The incubation was stopped by transferring the eppendorf tupe to an ice bath and adding 75 micro L solution to 75 micro L 0.5 M HEPES pH 7. 20 micro L of the above stopped solution was transferred into a microtiter plate and 200 micro L 3.7 mM 4,6-ethylidene-$G_7$PNP, 3.3 kU/L alpha-glucosidase, 52.2 mM HEPES, 73 mM NaCl, 10.5 mM MgCl2, 0.06 mM $CaCl_2$, pH 7 (AMYL kit, Roche Diagnostics GmbH). The absorbance at 405 nm was measured with 11 seconds intervals with a microplate reader (Spectra Max 190, Molecular Devices) and the activity was determined from the slope generated after 5 minutes measurement.

Figure 3:
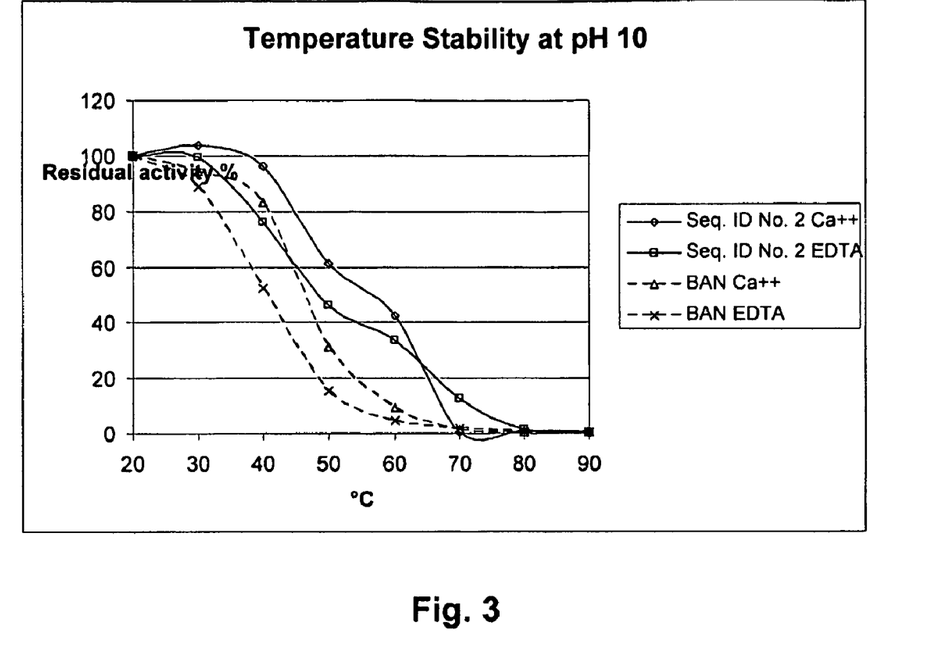
FIG. 3 shows the stability of the alpha-amylase of the invention after incubation at various temperatures.

The temperature stability is depicted in FIG. 3, where the stability of the amylase of the present invention is compared with the stability of the commercially available amylase BAN®, available from Novozymes A/S. FIG. 3 shows a superior stability of the amylase of the present invention as compared to the commercially available amylase.

pH Stability 150 micro L enzyme sample (diluted with 50 mM Britton-Robinson buffer (50 mM acetic acid, 50 mM phosphoric acid, 50 mM boric acid, pH adjusted to the value of interest with NaOH, with and without 1 mM $CaCl_2$)) in an Eppendorf tube was incubated for 30 minutes in a Eppendorf Thermomixer at 37° C. and 300 rpm shaking. The incubation was stopped by transferring 75 micro L solution to 75 micro L 0.5 M HEPES pH 7. 20 micro L of the above stopped solution was transferred into a microtiter plate and 200 μl 3.7 mM 4,6-ethylidene-$G_7$PNP, 3.3 kU/L alpha-glucosidase, 52.2 mM HEPES, 73 mM NaCl, 10.5 mM MgCl2, 0.06 mM $CaCl_2$, pH 7 (AMYL kit, Roche Diagnostics GmbH). The absorbance at 405 nm was measured with 11 seconds intervals with a micro plate reader (Spectra Max 190, Molecular Devices) and the activity was determined from the slope generated after 5 minutes measurement.

Figure 4:
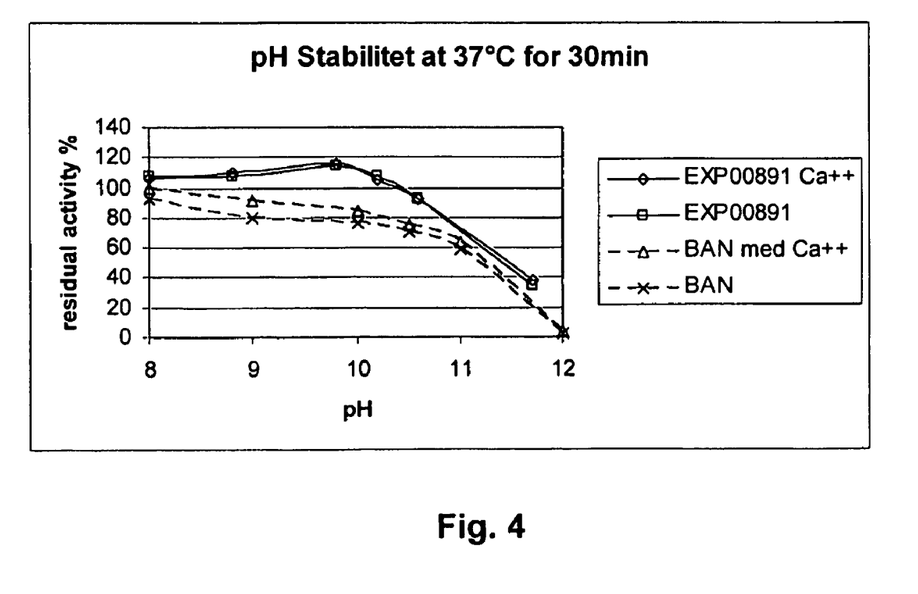
FIG. 4 shows the stability of the alpha-amylase of the invention after incubation at various pH.

The pH stability is depicted in FIG. 4, where the stability of the amylase of the present invention is compared with the stability of the commercially available amylase BAN®, available from Novozymes A/S. FIG. 4 shows a superior stability of the amylase of the present invention as compared to the commercially available amylase.

pH Determination

The pI of the polypeptide chain is determined theoretically by the pc program Vector NTI 8, 1994-2002 Infomax, Inc. pI was determined to 4.4.

Example 4

Amylose/Starch Degradation Pattern 20 micro L sample were added to 1 mL 1% amylose (Merck, 4561) or 1% waxy corn starch (Cerestar), 10 mM sodium borate buffer, 0.1 mM $CaCl_2$, pH 9 and incubated for various times at 37° C. The reaction was stopped by adding 20 micro L 1 M HCl and incubated at 95° C. for 10 minutes. The samples were filtered through a 0.22 micro meter filter and the carbohydrate composition was determined by IMPC HPLC.

The data below is expressed in % area in a top in the HPLC chromatogram, compared to total area of all oligosaccharides in the 1035 minutes chromatogram.

TABLE 1

Degradation pattern of 1% amylose.

1% amylose degradation pattern

|     | 0 min % | 17 min % | 45 min % | 120 min % | 1035 min % |
| --- | --- | --- | --- | --- | --- |
| DP6 | <1 | 3 | 5 | 8 | <1 |
| DP5 | <1 | 0 | 1 | 1 | <1 |
| DP4 | <1 | 2 | 6 | 15 | 48 |
| DP3 | <1 | <1 | <1 | 1 | 5 |
| DP2 | <1 | 1 | 2 | 6 | 26 |
| DP1 | <1 | 1 | 1 | 3 | 17 |

TABLE 2

Degradation pattern of 1% waxy corn starch.

1% waxy corn starch

|     | 0 min % | 17 min % | 45 min % | 120 min % | 1035 min % |
| --- | --- | --- | --- | --- | --- |
| DP6 | <1 | 8 | 11 | 8 | 2 |
| DP5 | <1 | <1 | 1 | 2 | 1 |
| DP4 | <1 | 3 | 7 | 18 | 30 |
| DP3 | <1 | <1 | <1 | <1 | 5 |
| DP2 | <1 | 1 | 3 | 8 | 19 |
| DP1 | <1 | 1 | 1 | 4 | 14 |

During amylose/amylopectin degradation no DP products larger than DP6 is seen. Initially the domination degradation product is DP6 and after prolonged incubation, this DP6 is hydrolysed to DP4 and DP2. Thus, this amylase exhibits substantially exo alpha amylase activity.

Example 5

Wash Performance of the Amylase of the Invention

Wash in Detergent Solution.

Washing performance is evaluated by washing starch-soiled CS-28 swatches (obtainable from CFT, Centre for Test Material, Netherlands) in a beaker under constant shaking.

4 g/L of a commercially available detergent (Mega Perls Color from Henkel GmbH) is added to water. Water hardness is adjusted to 15° dH by addition of Ca:Mg in the ratio 4:1 prior to the addition of the detergent. pH is not adjusted upon addition of detergent.

The soiled swatches are washed for 20 minutes at 40° C. Upon drying the reflectance is measured.

Figure 5:
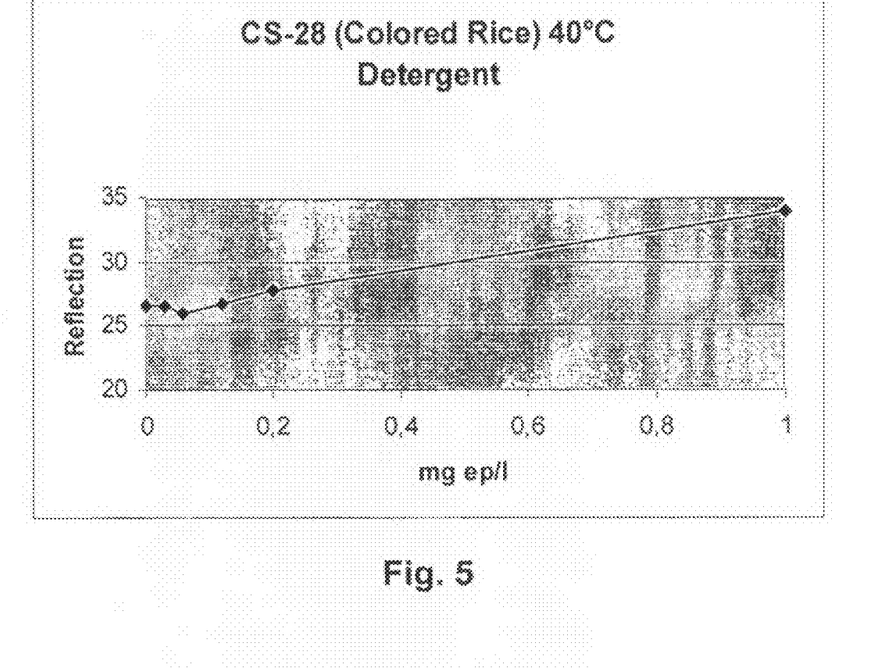
FIG. 5 shows the wash performance of the alpha-amylase in a commercial detergent.

As can be seen from FIG. 5 the alpha-amylase of the invention clearly is able to remove starch from the soiled swatches.

Wash in Buffer Solution.

Washing performance is evaluated by washing starch-soiled CS-28 swatches (obtainable from CFT, Centre for Test Material, Netherlands) in a beaker under constant shaking.

5 mM Carbonate buffer is used to adjust pH to 9.

The soiled swatches are washed for 20 minutes at 40° C. Upon drying the reflectance is measured.

Figure 6:
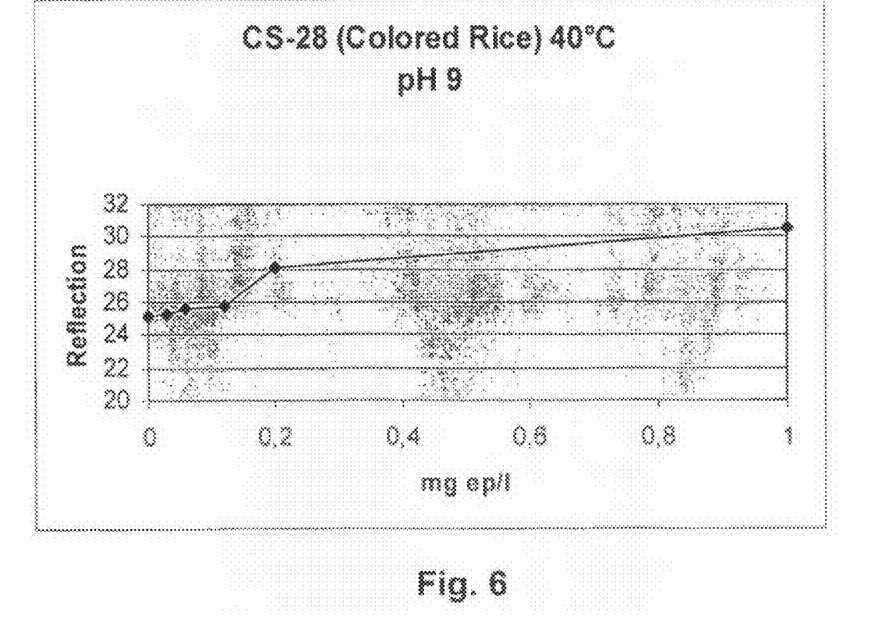
FIG. 6 shows the wash performance of the alpha-amylase at pH 9 in Carbonate buffer.

As can be seen from FIG. 6 the alpha-amylase of the invention clearly is able to remove starch from the soiled swatches.

---

The invention claimed is:

1. An isolated alpha-amylase comprising an amino acid sequence which has at least 95% identity with amino acids 1 to 1105 of SEQ ID NO: 2.

2. The alpha-amylase of claim 1, which comprises an amino acid sequence which has at least 97% identity with amino acids 1 to 1105 of SEQ ID NO: 2.

3. The alpha-amylase of claim 1, which comprises an amino acid sequence which has at least 98% identity with amino acids 1 to 1105 of SEQ ID NO: 2.

4. The alpha-amylase of claim 1, which comprises an amino acid sequence which has at least 99% identity with amino acids 1 to 1105 of SEQ ID NO: 2.

5. The alpha-amylase of claim 1, which comprises the amino acid sequence shown in SEQ ID NO: 2.

6. The alpha-amylase of claim 1, which consists of the amino acid sequence shown in SEQ ID NO: 2.

7. The alpha-amylase of claim 1 having one or more characteristics selected from the group consisting of:
   a) a theoretical pI of about 4.4;
   b) a pH-optimum of about 9.8;
   c) a temperature optimum of about 50° C. at pH 9;
   d) at least 40% residual activity after 30 minutes at 50° C. and pH 10; or
   e) obtained from *Bacillus* horikoshii.

8. An isolated alpha-amylase encoded by a nucleic acid sequence which hybridizes under high stringency conditions with the nucleic acid sequence of SEQ ID NO: 1, and/or the complete complementary strand of SEQ ID NO:1, wherein the high stringency conditions are defined as prehybridization and hybridization in 5×SSC, 5×Denhardt's solution, 0.5% SDS and 100 μg/ml of denatured sonicated salmon sperm DNA, followed by washing two times for 30 minutes using 2×SSC, 0.2% SDS at 70° C., wherein the hybridization occurs at 45° C.

9. An isolated DNA sequence encoding the alpha-amylase of claim 1.

10. The DNA sequence according to claim 9 which comprises the DNA sequence shown in positions 109-3423 of SEQ ID NO: 1.

11. A recombinant expression vector comprising the DNA sequence according to claim 9.

12. A detergent composition comprising the alpha-amylase of claim 1.

13. A cell transformed with a DNA sequence in accordance with claim 9.

14. A cell transformed with a recombinant expression vector of claim 11.

15. A cell in accordance with claim 13, wherein the cell is a bacterial, fungal or yeast cell.

16. A method of producing an alpha-amylase comprising: cultivating a cell transformed with a DNA sequence encoding an alpha-amylase comprising an amino acid sequence which has at least 95% identity with amino acids 1 to 1105 of SEQ ID NO: 2 under conditions permitting the production of the alpha-amylase.

17. The method of claim 16 further comprising recovering the alpha-amylase of the culture.

18. A method in accordance with claim 16 comprising cultivating an amylase producing strain of bacteria, fungi or yeast in a suitable nutrient medium, and recovering the alpha-amylase from the culture medium.

* * * * *

UNITED STATES PATENT AND TRADEMARK OFFICE
CERTIFICATE OF CORRECTION

PATENT NO. : 7,659,101 B2  Page 1 of 1
APPLICATION NO. : 11/721353
DATED : February 9, 2010
INVENTOR(S) : Hoff et al.

It is certified that error appears in the above-identified patent and that said Letters Patent is hereby corrected as shown below:

Title Page, paragraph Item (56) References Cited, please add

--UNITED STATES PATENT DOCUMENTS

US   5,147,796   9/1992--

Signed and Sealed this

Eleventh Day of May, 2010

David J. Kappos
*Director of the United States Patent and Trademark Office*

SEQUENCE LISTING

```
<160> NUMBER OF SEQ ID NOS: 2

<210> SEQ ID NO 1
<211> LENGTH: 3423
<212> TYPE: DNA
<213> ORGANISM: Bacillus horikoshii
<220> FEATURE:
<221> NAME/KEY: sig_peptide
<222> LOCATION: (1)..(108)
<220> FEATURE:
<221> NAME/KEY: CDS
<222> LOCATION: (109)..(3423)
<223> OTHER INFORMATION: mature peptide
      2881-3131 and 3160-3423 encodes starch binding domains

<400> SEQUENCE: 1
atgaacggtg taaaaaacg agtttcgatg tgtttgtttt ttgtatttgt tttagtagta        60
tcatcaataa tgccttatgt acaatcgagt atttccgtag tacaagcg gca gaa caa      117
                                                     Ala Glu Gln
                                                       1 aca gac aat ttc act tgg gat aat gca aca gtc tat ttt gcg atg acg      165
Thr Asp Asn Phe Thr Trp Asp Asn Ala Thr Val Tyr Phe Ala Met Thr
      5                  10                  15 gat cga ttt tac gat ggc aat cct tca aat aac aat tca tat ggc agg      213
Asp Arg Phe Tyr Asp Gly Asn Pro Ser Asn Asn Asn Ser Tyr Gly Arg
 20                  25                  30                  35 ccg caa caa gat gca tgg ggt caa aat ata ggg act ttc cat ggt ggg      261
Pro Gln Gln Asp Ala Trp Gly Gln Asn Ile Gly Thr Phe His Gly Gly
                  40                  45                  50 gac ctt caa ggg tta acc gac aaa tta aat gaa gga tac ttt act gac      309
```

```
                                                              -continued

Asp Leu Gln Gly Leu Thr Asp Lys Leu Asn Glu Gly Tyr Phe Thr Asp
        55                  60                  65 tta gga att aat gcg att tgg att acc gca cca tat gag caa ata cat       357
Leu Gly Ile Asn Ala Ile Trp Ile Thr Ala Pro Tyr Glu Gln Ile His
            70                  75                  80 ggt tgg gtt ggc ggt ggg tca gat ggt gat ttt gcc cat tat gct ttt       405
Gly Trp Val Gly Gly Gly Ser Asp Gly Asp Phe Ala His Tyr Ala Phe
        85                  90                  95 cac ggg tat tac gct ctt gac tac acg aca gtc gac caa aat atg gga       453
His Gly Tyr Tyr Ala Leu Asp Tyr Thr Thr Val Asp Gln Asn Met Gly
100                 105                 110                 115 act gta gag gaa atg cga gaa ttt gtt gat acc gca cat gaa aat ggc       501
Thr Val Glu Glu Met Arg Glu Phe Val Asp Thr Ala His Glu Asn Gly
                120                 125                 130 atc cgg gtt gtc ctt gat gtg gta atg aat cat cct ggc tac aac aca       549
Ile Arg Val Val Leu Asp Val Val Met Asn His Pro Gly Tyr Asn Thr
            135                 140                 145 tta aaa gat atg gag cag tat ggt ttt ggt acg caa caa tta aat tca       597
Leu Lys Asp Met Glu Gln Tyr Gly Phe Gly Thr Gln Gln Leu Asn Ser
        150                 155                 160 tct tgg act cct gga cct ggc caa aca tgg cat agc cac cac gaa caa       645
Ser Trp Thr Pro Gly Pro Gly Gln Thr Trp His Ser His His Glu Gln
165                 170                 175 att gat tat aat aat gcg aat gca tgg gca aat tgg tgg gga gat tgg       693
Ile Asp Tyr Asn Asn Ala Asn Ala Trp Ala Asn Trp Trp Gly Asp Trp
180                 185                 190                 195 att aga gct gat att ggt ggg tac gag aaa tgt ggt aat agt gaa att       741
Ile Arg Ala Asp Ile Gly Gly Tyr Glu Lys Cys Gly Asn Ser Glu Ile
                200                 205                 210 gaa atg tgt tta gct ggt tta cct gac ttt cgt acc gat tta act cat       789
Glu Met Cys Leu Ala Gly Leu Pro Asp Phe Arg Thr Asp Leu Thr His
            215                 220                 225 agt gtc ggg ttg ccg cca tta tta caa aca aaa tgg caa cag gaa tca       837
Ser Val Gly Leu Pro Pro Leu Leu Gln Thr Lys Trp Gln Gln Glu Ser
        230                 235                 240 agt ggt tat gaa aat tgg atc gtt cct gct gct agt aat tta cgt caa       885
Ser Gly Tyr Glu Asn Trp Ile Val Pro Ala Ala Ser Asn Leu Arg Gln
245                 250                 255 gat tta gga att gct ccg gct gat tat att gtg aaa tgg ctt tca gct       933
Asp Leu Gly Ile Ala Pro Ala Asp Tyr Ile Val Lys Trp Leu Ser Ala
260                 265                 270                 275 tgg gtt gag gaa ttt ggt att gat ggt ttt cgt gtc gat acg gca aaa       981
Trp Val Glu Glu Phe Gly Ile Asp Gly Phe Arg Val Asp Thr Ala Lys
                280                 285                 290 cat gtg gaa atg cac cgt tgg gac caa tta aag caa gcc gca aat gaa      1029
His Val Glu Met His Arg Trp Asp Gln Leu Lys Gln Ala Ala Asn Glu
            295                 300                 305 gca ctt tgg aca tgg cga gaa aat aat cca gat aag cct ggt gca aat      1077
Ala Leu Trp Thr Trp Arg Glu Asn Asn Pro Asp Lys Pro Gly Ala Asn
        310                 315                 320 tgg gat gat gat ttt tgg atg gtt gca gaa gta tgg ggc cat ggt gta      1125
Trp Asp Asp Asp Phe Trp Met Val Ala Glu Val Trp Gly His Gly Val
325                 330                 335 gga agg agc tca tat ttt gat cat ggt ttt gat tct gtc atc aat ttt      1173
Gly Arg Ser Ser Tyr Phe Asp His Gly Phe Asp Ser Val Ile Asn Phe
340                 345                 350                 355 acg ttc caa gga gaa cat ggc aat ggc cca gcg tat aat tta gcg aca      1221
Thr Phe Gln Gly Glu His Gly Asn Gly Pro Ala Tyr Asn Leu Ala Thr
                360                 365                 370
```

```
                                                     -continued atg gaa tca acg ttt tct cgt tat gcg cgt gac att aat tct gac cca      1269
Met Glu Ser Thr Phe Ser Arg Tyr Ala Arg Asp Ile Asn Ser Asp Pro
        375                 380                 385 tcg ttt aat gtg tta agt tat ata tca caa cat gat acg atg tta tac      1317
Ser Phe Asn Val Leu Ser Tyr Ile Ser Gln His Asp Thr Met Leu Tyr
390                 395                 400 ccg aga aat cgt ctt ctc gat ggt gga aca tat tta atg ttg tta cct      1365
Pro Arg Asn Arg Leu Leu Asp Gly Gly Thr Tyr Leu Met Leu Leu Pro
    405                 410                 415 ggg gca gtt caa gtg ttt tat gga gat gaa acg gcc cgt ccg ttc ggt      1413
Gly Ala Val Gln Val Phe Tyr Gly Asp Glu Thr Ala Arg Pro Phe Gly
420                 425                 430                 435 cca aca ggc tct gat tct cac caa gga aca cgt tct tcg atg aat tgg      1461
Pro Thr Gly Ser Asp Ser His Gln Gly Thr Arg Ser Ser Met Asn Trp
                440                 445                 450 ggt tca gtt aat gaa caa gtt ctt gaa cac tgg caa aag atg ggg caa      1509
Gly Ser Val Asn Glu Gln Val Leu Glu His Trp Gln Lys Met Gly Gln
            455                 460                 465 ttc cgt aat aat cat gtt tca ata gga gca ggg aaa cac aaa caa att      1557
Phe Arg Asn Asn His Val Ser Ile Gly Ala Gly Lys His Lys Gln Ile
        470                 475                 480 gga agc agt cca tat aca ttc agt cgt gta cat gat gac gat cga gtt      1605
Gly Ser Ser Pro Tyr Thr Phe Ser Arg Val His Asp Asp Asp Arg Val
485                 490                 495 gtt gtt tct atc ggt gcg agt ggt tct act aca att gat gtt tct tcc      1653
Val Val Ser Ile Gly Ala Ser Gly Ser Thr Thr Ile Asp Val Ser Ser
500                 505                 510                 515 gta ttt gat aac gga atg gaa tta cgg gac ttt tat aca ggg caa aca      1701
Val Phe Asp Asn Gly Met Glu Leu Arg Asp Phe Tyr Thr Gly Gln Thr
                520                 525                 530 gca aca gtt tca aat ggc cat gtg aca ttt gaa gct cat tct aat ggg      1749
Ala Thr Val Ser Asn Gly His Val Thr Phe Glu Ala His Ser Asn Gly
            535                 540                 545 gtt att tta att gaa caa gtg aaa tct gaa ctc ccg acc ctc tct gca      1797
Val Ile Leu Ile Glu Gln Val Lys Ser Glu Leu Pro Thr Leu Ser Ala
        550                 555                 560 aat cca ggt ggt gag gaa ttt gat aca gag gaa att gaa gtg gaa tta      1845
Asn Pro Gly Gly Glu Glu Phe Asp Thr Glu Glu Ile Glu Val Glu Leu
565                 570                 575 atg gtt tct gga gcg gaa caa gga tat tat acg att gat ggt tcc gat      1893
Met Val Ser Gly Ala Glu Gln Gly Tyr Tyr Thr Ile Asp Gly Ser Asp
580                 585                 590                 595 cct agc aaa gaa ggc att gcc ttt gct aac gga gat gtc att tca att      1941
Pro Ser Lys Glu Gly Ile Ala Phe Ala Asn Gly Asp Val Ile Ser Ile
                600                 605                 610 ggt gct aat tta gcg gtt gat gaa tcg ctc acc ttg aag tta ttt gct      1989
Gly Ala Asn Leu Ala Val Asp Glu Ser Leu Thr Leu Lys Leu Phe Ala
            615                 620                 625 gaa aat aaa atg gga agt gca acg gaa gaa tat aca ttt aca aaa aca      2037
Glu Asn Lys Met Gly Ser Ala Thr Glu Glu Tyr Thr Phe Thr Lys Thr
        630                 635                 640 cca cca tat gta agc gtt tct gca acc cct cct ggt gga aca ttt aca      2085
Pro Pro Tyr Val Ser Val Ser Ala Thr Pro Pro Gly Gly Thr Phe Thr
645                 650                 655 aca gag ttt gtt gaa atc aca tta aag tct aaa aat aca acg gat gct      2133
Thr Glu Phe Val Glu Ile Thr Leu Lys Ser Lys Asn Thr Thr Asp Ala
660                 665                 670                 675 ttt tac agt atc gat gga acc aat cca aag gat aat ggc att tct ttt      2181
Phe Tyr Ser Ile Asp Gly Thr Asn Pro Lys Asp Asn Gly Ile Ser Phe
                680                 685                 690
```

```
act gat ggg gag act att gtt atc ggt gag gaa gct act cat gga gat         2229
Thr Asp Gly Glu Thr Ile Val Ile Gly Glu Glu Ala Thr His Gly Asp
            695                 700                 705 gag ata aca tta cgg ctt tgg ggt caa aat gaa tac ggt gaa gtg gaa         2277
Glu Ile Thr Leu Arg Leu Trp Gly Gln Asn Glu Tyr Gly Glu Val Glu
    710                 715                 720 gaa cag tat acg tat aca aaa att gaa ggg ttg acc att cat ttc aaa         2325
Glu Gln Tyr Thr Tyr Thr Lys Ile Glu Gly Leu Thr Ile His Phe Lys
725                 730                 735 aaa cca tct tct tgg gga caa cca caa cta tat tac tat ggt aca aat         2373
Lys Pro Ser Ser Trp Gly Gln Pro Gln Leu Tyr Tyr Tyr Gly Thr Asn
740                 745                 750                 755 cca act gta tct gaa ccg aca tgg gca aac gca ccg aac atg gaa cat         2421
Pro Thr Val Ser Glu Pro Thr Trp Ala Asn Ala Pro Asn Met Glu His
                760                 765                 770 act ggt ggt gac tgg tat aaa tac aca att agc ggt gtt aaa gaa gcc         2469
Thr Gly Gly Asp Trp Tyr Lys Tyr Thr Ile Ser Gly Val Lys Glu Ala
            775                 780                 785 ttt gtt att ttt aaa gat aat caa gga aat caa aca cca gga caa agt         2517
Phe Val Ile Phe Lys Asp Asn Gln Gly Asn Gln Thr Pro Gly Gln Ser
        790                 795                 800 caa tca gga tat ttc cgt gat aaa gaa gga tgg tat gac ggt tct tgg         2565
Gln Ser Gly Tyr Phe Arg Asp Lys Glu Gly Trp Tyr Asp Gly Ser Trp
    805                 810                 815 cat aat caa aac cca gaa gag cca aca aaa cct gct tcc cct aaa aat         2613
His Asn Gln Asn Pro Glu Glu Pro Thr Lys Pro Ala Ser Pro Lys Asn
820                 825                 830                 835 ata gcc gtt cat gat gtc act gac aca aca gcg gtt att tca tgg gat         2661
Ile Ala Val His Asp Val Thr Asp Thr Thr Ala Val Ile Ser Trp Asp
                840                 845                 850 gtt gtc act ggt gct gtc gaa ggg tac cga tta tat gat gaa gat aat         2709
Val Val Thr Gly Ala Val Glu Gly Tyr Arg Leu Tyr Asp Glu Asp Asn
            855                 860                 865 aat gtt gta caa gaa aca aca aac gaa acg att aca tta gaa aac ctt         2757
Asn Val Val Gln Glu Thr Thr Asn Glu Thr Ile Thr Leu Glu Asn Leu
        870                 875                 880 acg tct gaa acg gaa tat tct ttt tac gtc acc gct ttt aat tcg gtt         2805
Thr Ser Glu Thr Glu Tyr Ser Phe Tyr Val Thr Ala Phe Asn Ser Val
    885                 890                 895 ggg gaa tcc gaa cga agt gaa caa att gca ttc act aca aaa aga aca         2853
Gly Glu Ser Glu Arg Ser Glu Gln Ile Ala Phe Thr Thr Lys Arg Thr
900                 905                 910                 915 aac ata gga aaa aac gaa gtg act att tat tat aat gga ttt gaa gct         2901
Asn Ile Gly Lys Asn Glu Val Thr Ile Tyr Tyr Asn Gly Phe Glu Ala
                920                 925                 930 cct tat att cat tat aaa ccg gtt gga gga atg tgg aca aca gta ccc         2949
Pro Tyr Ile His Tyr Lys Pro Val Gly Gly Met Trp Thr Thr Val Pro
            935                 940                 945 ggg gaa gcg atg tca cct tct gat aaa cct ggg ttt tcg aaa att aca         2997
Gly Glu Ala Met Ser Pro Ser Asp Lys Pro Gly Phe Ser Lys Ile Thr
        950                 955                 960 att aat gtt ggg gat gct gac gga att gtc gct gca ttt aat aac ggt         3045
Ile Asn Val Gly Asp Ala Asp Gly Ile Val Ala Ala Phe Asn Asn Gly
    965                 970                 975 cat ggt caa tgg gat aat aat caa gga cag gat tat acg ttt ggt tta         3093
His Gly Gln Trp Asp Asn Asn Gln Gly Gln Asp Tyr Thr Phe Gly Leu
980                 985                 990                 995 ggt acg ttt acc gta  atg aac ggt aaa att  agt gaa ggc gaa cct           3138
Gly Thr Phe Thr Val  Met Asn Gly Lys Ile  Ser Glu Gly Glu Pro
```

-continued

```
               1000                1005                1010
acg aat cag ttc  act  caa att tat  tac caa  aca ggc tgg tcg aat              3183
Thr Asn Gln Phe  Thr  Gln Ile Tyr  Tyr Gln  Thr Gly Trp Ser Asn
                 1015                1020                1025 ccg cat att cat tat  gct atc gat  ggt  caa tgg aca cag tca                   3228
Pro His Ile His Tyr  Ala Ile Asp  Gly  Gln Trp Thr Gln Ser
                1030              1035                1040 cct ggt gtc aga atg  caa cgt tct tct  gaa tat aca gga tat tct                3273
Pro Gly Val Arg Met  Gln Arg Ser Ser  Glu Tyr Thr Gly Tyr Ser
                1045                 1050                1055 gtt gta acg att gat  gta ggc tca cga  agt  ggt ctc acc gct gtc               3318
Val Val Thr Ile Asp  Val Gly Ser Arg  Ser  Gly Leu Thr Ala Val
                1060                 1065                1070 ttt aat aac gga agt  ggt caa tgg gat aat  aac caa ggc cga aac                3363
Phe Asn Asn Gly Ser  Gly Gln Trp Asp Asn  Asn Gln Gly Arg Asn
                1075                1080                1085 tat caa ttt ggg aca  ggg att tac aca ctt  tca tca gga aga atc                3408
Tyr Gln Phe Gly Thr  Gly Ile Tyr Thr Leu  Ser Ser Gly Arg Ile
                1090                1095                1100 ata gaa ggg aca cct                                                          3423
Ile Glu Gly Thr Pro
                1105

<210> SEQ ID NO 2
<211> LENGTH: 1105
<212> TYPE: PRT
<213> ORGANISM: Bacillus horikoshii

<400> SEQUENCE: 2

Ala Glu Gln Thr Asp Asn Phe Thr Trp Asp Asn Ala Thr Val Tyr Phe
1               5                   10                  15

Ala Met Thr Asp Arg Phe Tyr Asp Gly Asn Pro Ser Asn Asn Asn Ser
                20                  25                  30

Tyr Gly Arg Pro Gln Gln Asp Ala Trp Gly Gln Asn Ile Gly Thr Phe
            35                  40                  45

His Gly Gly Asp Leu Gln Gly Leu Thr Asp Lys Leu Asn Glu Gly Tyr
        50                  55                  60

Phe Thr Asp Leu Gly Ile Asn Ala Ile Trp Ile Thr Ala Pro Tyr Glu
65                  70                  75                  80

Gln Ile His Gly Trp Val Gly Gly Ser Asp Gly Asp Phe Ala His
                85                  90                  95

Tyr Ala Phe His Gly Tyr Tyr Ala Leu Asp Tyr Thr Thr Val Asp Gln
                100                 105                 110

Asn Met Gly Thr Val Glu Glu Met Arg Glu Phe Val Asp Thr Ala His
            115                 120                 125

Glu Asn Gly Ile Arg Val Val Leu Asp Val Val Met Asn His Pro Gly
        130                 135                 140

Tyr Asn Thr Leu Lys Asp Met Glu Gln Tyr Gly Phe Gly Thr Gln Gln
145                 150                 155                 160

Leu Asn Ser Ser Trp Thr Pro Gly Pro Gly Gln Thr Trp His Ser His
                165                 170                 175

His Glu Gln Ile Asp Tyr Asn Asn Ala Asn Ala Trp Ala Asn Trp Trp
            180                 185                 190

Gly Asp Trp Ile Arg Ala Asp Ile Gly Gly Tyr Glu Lys Cys Gly Asn
        195                 200                 205

Ser Glu Ile Glu Met Cys Leu Ala Gly Leu Pro Asp Phe Arg Thr Asp
    210                 215                 220
```

```
Leu Thr His Ser Val Gly Leu Pro Pro Leu Leu Gln Thr Lys Trp Gln
225                 230                 235                 240

Gln Glu Ser Ser Gly Tyr Glu Asn Trp Ile Val Pro Ala Ala Ser Asn
                245                 250                 255

Leu Arg Gln Asp Leu Gly Ile Ala Pro Ala Asp Tyr Ile Val Lys Trp
            260                 265                 270

Leu Ser Ala Trp Val Glu Glu Phe Gly Ile Asp Gly Phe Arg Val Asp
        275                 280                 285

Thr Ala Lys His Val Glu Met His Arg Trp Asp Gln Leu Lys Gln Ala
    290                 295                 300

Ala Asn Glu Ala Leu Trp Thr Trp Arg Glu Asn Asn Pro Asp Lys Pro
305                 310                 315                 320

Gly Ala Asn Trp Asp Asp Phe Trp Met Val Ala Glu Val Trp Gly
                325                 330                 335

His Gly Val Gly Arg Ser Ser Tyr Phe Asp His Gly Phe Asp Ser Val
                340                 345                 350

Ile Asn Phe Thr Phe Gln Gly Glu His Gly Asn Gly Pro Ala Tyr Asn
                355                 360                 365

Leu Ala Thr Met Glu Ser Thr Phe Ser Arg Tyr Ala Arg Asp Ile Asn
    370                 375                 380

Ser Asp Pro Ser Phe Asn Val Leu Ser Tyr Ile Ser Gln His Asp Thr
385                 390                 395                 400

Met Leu Tyr Pro Arg Asn Arg Leu Leu Asp Gly Gly Thr Tyr Leu Met
                405                 410                 415

Leu Leu Pro Gly Ala Val Gln Val Phe Tyr Gly Asp Glu Thr Ala Arg
                420                 425                 430

Pro Phe Gly Pro Thr Gly Ser Asp Ser His Gln Gly Thr Arg Ser Ser
            435                 440                 445

Met Asn Trp Gly Ser Val Asn Glu Gln Val Leu Glu His Trp Gln Lys
450                 455                 460

Met Gly Gln Phe Arg Asn Asn His Val Ser Ile Gly Ala Gly Lys His
465                 470                 475                 480

Lys Gln Ile Gly Ser Ser Pro Tyr Thr Phe Ser Arg Val His Asp Asp
                485                 490                 495

Asp Arg Val Val Val Ser Ile Gly Ala Ser Gly Ser Thr Thr Ile Asp
            500                 505                 510

Val Ser Ser Val Phe Asp Asn Gly Met Glu Leu Arg Asp Phe Tyr Thr
        515                 520                 525

Gly Gln Thr Ala Thr Val Ser Asn Gly His Val Thr Phe Glu Ala His
    530                 535                 540

Ser Asn Gly Val Ile Leu Ile Glu Gln Val Lys Ser Glu Leu Pro Thr
545                 550                 555                 560

Leu Ser Ala Asn Pro Gly Gly Glu Glu Phe Asp Thr Glu Ile Glu
                565                 570                 575

Val Glu Leu Met Val Ser Gly Ala Glu Gln Gly Tyr Tyr Thr Ile Asp
                580                 585                 590

Gly Ser Asp Pro Ser Lys Glu Gly Ile Ala Phe Ala Asn Gly Asp Val
            595                 600                 605

Ile Ser Ile Gly Ala Asn Leu Ala Val Asp Glu Ser Leu Thr Leu Lys
        610                 615                 620

Leu Phe Ala Glu Asn Lys Met Gly Ser Ala Thr Glu Glu Tyr Thr Phe
625                 630                 635                 640
```

```
Thr Lys Thr Pro Pro Tyr Val Ser Val Ser Ala Thr Pro Gly Gly
            645                 650                 655

Thr Phe Thr Thr Glu Phe Val Glu Ile Thr Leu Lys Ser Lys Asn Thr
                660                 665                 670

Thr Asp Ala Phe Tyr Ser Ile Asp Gly Thr Asn Pro Lys Asp Asn Gly
            675                 680                 685

Ile Ser Phe Thr Asp Gly Glu Thr Ile Val Ile Gly Glu Glu Ala Thr
690                 695                 700

His Gly Asp Glu Ile Thr Leu Arg Leu Trp Gly Gln Asn Glu Tyr Gly
705                 710                 715                 720

Glu Val Glu Glu Gln Tyr Thr Tyr Thr Lys Ile Glu Gly Leu Thr Ile
                725                 730                 735

His Phe Lys Lys Pro Ser Ser Trp Gly Gln Pro Gln Leu Tyr Tyr Tyr
            740                 745                 750

Gly Thr Asn Pro Thr Val Ser Glu Pro Thr Trp Ala Asn Ala Pro Asn
            755                 760                 765

Met Glu His Thr Gly Gly Asp Trp Tyr Lys Tyr Thr Ile Ser Gly Val
770                 775                 780

Lys Glu Ala Phe Val Ile Phe Lys Asp Asn Gly Asn Gln Thr Pro
785                 790                 795                 800

Gly Gln Ser Gln Ser Gly Tyr Phe Arg Asp Lys Glu Gly Trp Tyr Asp
            805                 810                 815

Gly Ser Trp His Asn Gln Asn Pro Glu Glu Pro Thr Lys Pro Ala Ser
            820                 825                 830

Pro Lys Asn Ile Ala Val His Asp Val Thr Asp Thr Ala Val Ile
            835                 840                 845

Ser Trp Asp Val Val Thr Gly Ala Val Glu Gly Tyr Arg Leu Tyr Asp
            850                 855                 860

Glu Asp Asn Asn Val Val Gln Glu Thr Thr Asn Glu Thr Ile Thr Leu
865                 870                 875                 880

Glu Asn Leu Thr Ser Glu Thr Glu Tyr Ser Phe Tyr Val Thr Ala Phe
                885                 890                 895

Asn Ser Val Gly Glu Ser Glu Arg Ser Glu Gln Ile Ala Phe Thr Thr
            900                 905                 910

Lys Arg Thr Asn Ile Gly Lys Asn Glu Val Thr Ile Tyr Tyr Asn Gly
            915                 920                 925

Phe Glu Ala Pro Tyr Ile His Tyr Lys Pro Val Gly Gly Met Trp Thr
930                 935                 940

Thr Val Pro Gly Glu Ala Met Ser Pro Ser Asp Lys Pro Gly Phe Ser
945                 950                 955                 960

Lys Ile Thr Ile Asn Val Gly Asp Ala Asp Gly Ile Val Ala Ala Phe
            965                 970                 975

Asn Asn Gly His Gly Gln Trp Asp Asn Asn Gln Gly Gly Asp Tyr Thr
            980                 985                 990

Phe Gly Leu Gly Thr Phe Thr Val Met Asn Gly Lys Ile Ser Glu Gly
                995                 1000                1005

Glu Pro Thr Asn Gln Phe Thr Gln Ile Tyr Tyr Gln Thr Gly Trp
    1010                1015                1020

Ser Asn Pro His Ile His Tyr Ala Ile Asp Gly Gly Gln Trp Thr
    1025                1030                1035

Gln Ser Pro Gly Val Arg Met Gln Arg Ser Ser Glu Tyr Thr Gly
    1040                1045                1050

Tyr Ser Val Val Thr Ile Asp Val Gly Ser Arg Ser Gly Leu Thr
```

-continued

```
              1055                1060                1065
Ala Val Phe Asn Asn Gly Ser Gly Gln Trp Asp Asn Asn Gln Gly
    1070                1075                1080

Arg Asn Tyr Gln Phe Gly Thr Gly Ile Tyr Thr Leu Ser Ser Gly
    1085                1090                1095

Arg Ile Ile Glu Gly Thr Pro
    1100                1105
```